United States Patent
Komiya

(10) Patent No.: US 10,179,848 B2
(45) Date of Patent: Jan. 15, 2019

(54) TIRE MEMBER MANUFACTURING METHOD AND TIRE MANUFACTURING METHOD

(71) Applicant: TOYO TIRE & RUBBER CO., LTD., Itami-shi, Hyogo (JP)

(72) Inventor: Yuki Komiya, Itami (JP)

(73) Assignee: TOYO TIRE & RUBBER CO., LTD., Itami-shi (JP)

( * ) Notice: Subject to any disclaimer, the term of this patent is extended or adjusted under 35 U.S.C. 154(b) by 0 days.

(21) Appl. No.: 15/685,383

(22) Filed: Aug. 24, 2017

(65) Prior Publication Data
US 2018/0105676 A1 Apr. 19, 2018

(30) Foreign Application Priority Data
Oct. 14, 2016 (JP) .................. 2016-202822

(51) Int. Cl.
| | |
|---|---|
| *C08K 5/20* | (2006.01) |
| *B60C 1/00* | (2006.01) |
| *C07C 233/44* | (2006.01) |
| *C07C 235/28* | (2006.01) |
| *C08K 5/17* | (2006.01) |
| *C08K 5/18* | (2006.01) |
| *C08L 9/08* | (2006.01) |
| *C08L 11/02* | (2006.01) |
| *C08L 15/00* | (2006.01) |

(52) U.S. Cl.
CPC .............. *C08K 5/20* (2013.01); *B60C 1/00* (2013.01); *C07C 233/44* (2013.01); *C07C 235/28* (2013.01); *C08K 5/175* (2013.01); *C08K 5/18* (2013.01); *C08L 9/08* (2013.01); *C08L 11/02* (2013.01); *C08L 15/005* (2013.01)

(58) Field of Classification Search
CPC .. C08K 5/125; C08K 5/18; C08K 5/20; B60C 1/00

USPC ................................................ 523/335, 351
See application file for complete search history.

(56) References Cited

U.S. PATENT DOCUMENTS

2014/0128532 A1   5/2014 Nakamura et al.

FOREIGN PATENT DOCUMENTS

JP           2014-95013 A    5/2014

*Primary Examiner* — Edward J Cain
(74) *Attorney, Agent, or Firm* — Westerman, Hattori, Daniels & Adrian, LLP

(57) ABSTRACT

A first tire member manufacturing method includes an operation in which a master batch is made, and an operation in which the master batch, peptizing agent, and processing additive are mixed. The operation in which the master batch is made includes an operation in which carbon-black-containing pre-coagulation rubber latex is coagulated to obtain a coagulum, an operation in which a compound according to Formula (I), below, is added to the water-containing coagulum, and an operation in which the compound according to Formula (I) is dispersed within the coagulum.

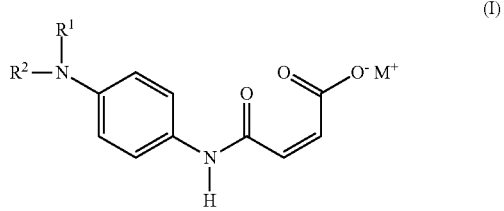

In Formula (I), $R^1$ and $R^2$ each indicates a hydrogen atom, an alkyl group having 1 to 20 carbons, an alkenyl group having 1 to 20 carbons, or an alkynyl group having 1 to 20 carbons. $R^1$ and $R^2$ may be the same or different. $M^+$ indicates sodium ion, potassium ion, or lithium ion.

6 Claims, No Drawings

TIRE MEMBER MANUFACTURING METHOD AND TIRE MANUFACTURING METHOD

TECHNICAL FIELD

The present invention relates to a tire member manufacturing method and a tire manufacturing method.

BACKGROUND ART

Patent Reference No. 1 discloses a method in which (2Z)-4-[(4-aminophenyl)amino]-4-oxo-2-butene acid sodium and carbon black are placed in a Banbury mixer and kneaded with rubber (hereinafter "prior manufacturing method"). Regarding (2Z)-4-[(4-aminophenyl)amino]-4-oxo-2-butene acid sodium, Patent Reference No. 1 further discloses that the terminal nitrogen functional group bonds to carbon black and that the carbon-carbon double-bond portion bonds to polymer.

PRIOR ART REFERENCES

Patent References

PATENT REFERENCE NO. 1: Japanese Patent Application Publication Kokai No. 2014-95013

SUMMARY OF INVENTION

Means for Solving Problem

A first tire member manufacturing method in accordance with the present disclosure comprises an operation in which master batch is made, and an operation in which the master batch, peptizing agent, and processing additive are mixed. The operation in which the master batch is made comprises an operation in which carbon-black-containing pre-coagulation rubber latex is coagulated to obtain a coagulum. The operation in which the master batch is made further comprises an operation in which a compound according to Formula (I) (hereinafter "the compound according to Formula (I)"), below, is added to the water-containing coagulum. The operation in which the master batch is made further comprises an operation in which the compound according to Formula (I) is dispersed within the coagulum.

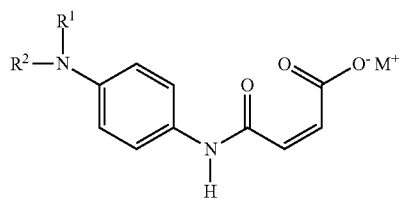

(I)

(At Formula (I), $R^1$ and $R^2$ each indicates a hydrogen atom, an alkyl group having 1 to 20 carbons, an alkenyl group having 1 to 20 carbons, or an alkynyl group having 1 to 20 carbons. $R^1$ and $R^2$ may be the same or different. $M^+$ indicates sodium ion, potassium ion, or lithium ion.)

A second tire member manufacturing method in accordance with the present disclosure comprises an operation in which master batch is made, and an operation in which the master batch, peptizing agent, and processing additive are mixed. The operation in which the master batch is made comprises an operation in which a compound according to Formula (I) is added to a mixture comprising carbon black and rubber, and an operation in which the compound according to Formula (I) is dispersed within the mixture in the presence of water.

EMBODIMENTS FOR CARRYING OUT INVENTION

There are situations in which unvulcanized rubber is used after being stored. Storage of unvulcanized rubber may cause increase in Mooney viscosity.

The present disclosure provides a tire member manufacturing method capable of inhibiting increase in Mooney viscosity that might otherwise occur as a result of storage thereof The present disclosure further provides a tire manufacturing method capable of inhibiting increase in Mooney viscosity that might otherwise occur as a result of storage thereof.

A first tire member manufacturing method comprises an operation in which master batch is made, and an operation in which the master batch, peptizing agent, and processing additive are mixed. The operation in which the master batch is made comprises an operation in which carbon-black-containing pre-coagulation rubber latex is coagulated to obtain a coagulum. The operation in which the master batch is made further comprises an operation in which a compound according to Formula (I) is added to the water-containing coagulum. The operation in which the master batch is made further comprises an operation in which the compound according to Formula (I) is dispersed within the coagulum.

The first tire member manufacturing method permits greater inhibition of increase in Mooney viscosity due to storage than the prior manufacturing method. This is so firstly because the first tire member manufacturing method permits a high degree of dispersal of the compound according to Formula (I), which has antioxidative capability. This is so secondly because it permits rubber originating from the master batch and the compound according to Formula (I) to be satisfactorily reacted.

The first tire member manufacturing method makes it possible for the compound according to Formula (I) to be dispersed to a high degree within rubber originating from the master batch. Because the compound according to Formula (I) is hydrophilic and because rubber in its dried state is hydrophobic, the compound according to Formula (I) tends not to be easily dispersed by the prior manufacturing method. In contrast, with the first tire member manufacturing method, the water content of the coagulum may facilitate dispersal of the compound according to Formula (I). The first tire member manufacturing method therefore permits more improvement in the dispersion characteristics of the compound according to Formula (I) than the prior manufacturing method.

The first tire member manufacturing method permits rubber originating from the master batch and the compound according to Formula (I) to be satisfactorily reacted. This is so because it permits radicals that will become reaction sites for the compound according to Formula (I) to be produced as a result of polymer chain scission caused by the peptizing agent.

Moreover, the first tire member manufacturing method permits increase in Mooney viscosity that might otherwise occur due to the compound according to Formula (I) to be inhibited by the processing additive.

At the first tire member manufacturing method, the operation in which the master batch is made may further comprise, prior to the operation in which carbon-black-containing pre-coagulation rubber latex is coagulated to obtain a coagulum, an operation in which carbon black and a first rubber latex are mixed to obtain a carbon black slurry, and an operation in which the carbon black slurry and a second rubber latex are mixed to obtain the pre-coagulation rubber latex.

At the first tire member manufacturing method, it is preferred that the operation in which the compound according to Formula (I) is dispersed within the coagulum be an operation in which the compound according to Formula (I) is dispersed within the coagulum as the coagulum is being dewatered.

At the first tire member manufacturing method, at the operation in which the compound according to Formula (I) is added to the coagulum, taking the amount of water in the coagulum for every 100 parts by mass of rubber within the coagulum to be Wa, and taking the amount of compound according to Formula (I) that is added for every 100 parts by mass of rubber within the coagulum to be Wb, it is preferred that the ratio of Wa to Wb (i.e., Wa/Wb) be in the range 1 to 8100.

A first tire manufacturing method may comprise the first tire member manufacturing method.

A second tire member manufacturing method comprises an operation in which master batch is made, and an operation in which the master batch, peptizing agent, and processing additive are mixed. The operation in which the master batch is made comprises an operation in which a compound according to Formula (I) is added to a mixture comprising carbon black and rubber, and an operation in which the compound according to Formula (I) is dispersed within the mixture in the presence of water.

The second tire member manufacturing method permits greater inhibition of increase in Mooney viscosity due to storage than the prior manufacturing method. This is so firstly because the second tire member manufacturing method permits a high degree of dispersal of the compound according to Formula (I), which has antioxidative capability. This is so secondly because it permits rubber originating from the master batch and the compound according to Formula (I) to be satisfactorily reacted. Moreover, the second tire member manufacturing method also permits increase in Mooney viscosity that might otherwise occur due to the compound according to Formula (I) to be inhibited by the processing additive.

A second tire manufacturing method may comprise the second tire member manufacturing method.

A tire member manufacturing method in accordance with a first embodiment comprises an operation in which carbon black and rubber latex are mixed to obtain a carbon black slurry. Mixing the carbon black and the rubber latex makes it is possible to prevent reflocculation of carbon black. This is thought to be due to formation of an extremely thin latex phase on all or part of the surface of the carbon black, the latex phase inhibiting reflocculation of carbon black. As examples of the carbon black, besides SAF, ISAF, HAF, FEF, GPF, and other such carbon blacks ordinarily used in the rubber industry, acetylene black, Ketchen black, and/or other such electrically conductive carbon blacks may be used. The carbon black may be nongranulated carbon black or may be granulated carbon black that has been granulated based upon considerations related to the handling characteristics thereof as is ordinary practice in the rubber industry. The rubber latex at the operation in which the carbon black slurry is made may for example be natural rubber latex, synthetic rubber latex, and/or the like. The number average molecular weight of natural rubber within the natural rubber latex might, for example, be not less than 2,000,000. The synthetic rubber latex might, for example, be styrene-butadiene rubber latex, butadiene rubber latex, nitrile rubber latex, and/or chloroprene rubber latex. It is preferred that solids (rubber) concentration in the rubber latex be not less than 0.1 mass %, more preferred that this be not less than 0.2 mass %, and still more preferred that this be not less than 0.3 mass %. The upper limit of the range in values for the solids concentration might, for example, be 5 mass %, it being preferred that this be 2 mass %, and it being more preferred that this be 1 mass %. The carbon black and the rubber latex may be mixed using a high-shear mixer, high shear mixer, homomixer, ball mill, bead mill, high-pressure homogenizer, ultrasonic homogenizer, colloid mill, and/or other such ordinary disperser.

In the carbon black slurry, carbon black is dispersed in water. It is preferred that the amount of carbon black in the carbon black slurry be not less than 1 mass %, and more preferred that this be not less than 3 mass %, per 100 mass % of the carbon black slurry. It is preferred that the upper limit of the range in values for the amount of carbon black in the carbon black slurry be 15 mass %, and more preferred that this be 10 mass %.

The tire member manufacturing method in accordance with the first embodiment further comprises an operation in which the carbon black slurry and rubber latex are mixed to obtain pre-coagulation rubber latex. The rubber latex for mixture with the carbon black slurry may for example be natural rubber latex, synthetic rubber latex, and/or the like. It is preferred that the solids concentration of the rubber latex for mixture with the carbon black slurry be greater than the solids concentration of the rubber latex at the operation in which the carbon black slurry is made. It is preferred that the solids concentration of the rubber latex for mixture with the carbon black slurry be not less than 10 mass %, and more preferred that this be not less than 20 mass %. The upper limit of the range in values for the solids concentration at the rubber latex might, for example, be 60 mass %, it being preferred that this be 40 mass %, and it being more preferred that this be 30 mass %. The carbon black slurry and the rubber latex may be mixed using a high-shear mixer, high shear mixer, homomixer, ball mill, bead mill, high-pressure homogenizer, ultrasonic homogenizer, colloid mill, and/or other such ordinary disperser.

In the pre-coagulation rubber latex, rubber particles, carbon black, and so forth are dispersed in water.

The tire member manufacturing method in accordance with the first embodiment further comprises an operation in which the pre-coagulation rubber latex is coagulated to obtain a coagulum. Coagulant may be added to the pre-coagulation rubber latex to cause it to coagulate. The coagulant might, for example, be an acid. As the acid, formic acid, sulfuric acid, and the like may be cited as examples. The coagulum obtained by coagulation of the pre-coagulation rubber latex contains water.

The tire member manufacturing method in accordance with the first embodiment further comprises an operation in which a compound according to Formula (I) is added to the coagulum. At the operation in which the compound according to Formula (I) is added, the amount Wa of water in the coagulum might, for example, be not less than 1 part by mass, it being preferred that this be not less than 10 parts by mass, for every 100 parts by mass of rubber within the coagulum. The upper limit of the range in values for Wa might, for example, be 800 parts by mass, it being preferred that this be 600 parts by mass. The amount Wb of compound according to Formula (I) that is added might, for example, be not less than 0.1 part by mass, it being preferred that this be not less than 0.5 part by mass, for every 100 parts by mass of rubber within the coagulum. The upper limit of the range in values for Wb might, for example, be 10 parts by mass, it being preferred that this be 5 parts by mass. It is preferred that the ratio of Wa to Wb (i.e., Wa/Wb) be in the range 1 to 8100. Causing Wa/Wb to be less than 1 would be unlikely to produce much benefit in terms of improvement of fatigue resistance. Above 8100, it might be the case that the water content of the coagulum will remain in the master batch.

Formula (I) is indicated below.

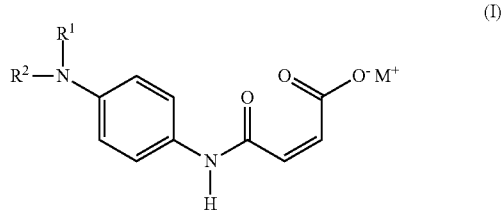

(I)

(At Formula (I), $R^1$ and $R^2$ each indicates a hydrogen atom, an alkyl group having 1 to 20 carbons, an alkenyl group having 1 to 20 carbons, or an alkynyl group having 1 to 20 carbons. $R^1$ and $R^2$ may be the same or different. $M^+$ indicates sodium ion, potassium ion, or lithium ion.)

At Formula (I), it is preferred that $R^1$ and $R^2$ each be a hydrogen atom. It is preferred that $M^+$ be a sodium ion. It is preferred that the compound according to Formula (I) be a compound according to Formula (I'), below.

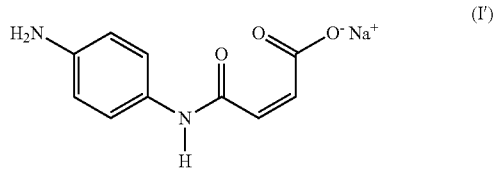

(I')

The tire member manufacturing method in accordance with the first embodiment further comprises an operation in which the compound according to Formula (I) is dispersed within the coagulum. The operation in which the compound according to Formula (I) is dispersed within the coagulum might, for example, be an operation in which the compound according to Formula (I) is dispersed within the coagulum as the post-addition-of-compound-according-to-Formula-(I) coagulum is being dewatered; more specifically, this might be an operation in which the compound according to Formula (I) is dispersed within the coagulum as a shear force is imparted at 100° C. to 250° C. to the post-addition-of-compound-according-to-Formula-(I) coagulum. It is preferred that the lower limit of the range in values for temperature be 120° C. It is preferred that the upper limit of the range in values for temperature be 230° C. A single screw extruder or other such extruder may be used for dispersing the compound according to Formula (I) within the coagulum.

The tire member manufacturing method in accordance with the first embodiment further comprises an operation in which, following dispersal of the compound according to Formula (I), drying and plasticization of the coagulum are carried out to obtain a master batch.

The master batch comprises rubber. The rubber might, for example, be natural rubber, isoprene rubber, butadiene rubber, styrene-butadiene rubber, nitrile rubber, chloroprene rubber, and/or the like. It is preferred that the amount of natural rubber in the master batch be not less than 70 mass %, more preferred that this be not less than 80 mass %, still more preferred that this be not less than 90 mass %, and still more preferred that this be 100 mass %, per 100 mass % of the rubber.

The master batch further comprises carbon black. For every 100 parts by mass of the rubber, it is preferred that the amount of carbon black be not less than 10 parts by mass, more preferred that this be not less than 20 parts by mass, and still more preferred that this be not less than 30 parts by mass. For every 100 parts by mass of the rubber, it is preferred that the amount of carbon black be not greater than 80 parts by mass, and more preferred that this be not greater than 60 parts by mass.

The master batch further comprises a compound according to Formula (I). For every 100 parts by mass of the rubber, it is preferred that the amount of the compound according to Formula (I) be not less than 0.1 part by mass, more preferred that this be not less than 0.5 part by mass, and still more preferred that this be not less than 1 part by mass. For every 100 parts by mass of the rubber, it is preferred that the amount of the compound according to Formula (I) be not greater than 10 parts by mass, and more preferred that this be not greater than 8 parts by mass.

The tire member manufacturing method in accordance with the first embodiment further comprises an operation in which master batch, and peptizing agent, processing additive, and/or other such compounding ingredients—and, where necessary, rubber not originating from the master batch—are dry-blended in a mixer to obtain a mixture. As rubber not originating from the master batch, natural rubber, isoprene rubber, butadiene rubber, styrene-butadiene rubber, nitrile rubber, chloroprene rubber, and the like may be cited as examples. The peptizing agent may cause radicals to be produced as a result of scission of rubber component polymer chains. 2,2'-Dibenzamidodiphenyl disulfide (DBD), zinc salts of 2-benzamidothiophenol, xylyl mercaptan, β-naphthyl mercaptan, pentachlorothiophenol (PCTP), and the like may be cited as examples. Of these, DBD is preferred. Any one of these may be used alone, or two or more of these may be used in combination. For every 100 parts by mass of total rubber ("total rubber" comprises rubber originating from the master batch and rubber not originating from the master batch), the amount of peptizing agent that is added might, for example, be not less than 0.01 part by mass, it being preferred that this be not less than 0.05 part by mass. For every 100 parts by mass of total rubber, the upper limit of the range in values for the amount of peptizing agent that is added might, for example, be 3 parts by mass, it being preferred that this be 2 parts by mass, and it being more preferred that this be 1 part by mass. If too much peptizing agent is added, there is a possibility that this may cause decrease in storage stability. The processing additive may comprise fatty acid metal salt(s). The fatty acid of the fatty acid metal salt is preferably a saturated or unsaturated fatty acid having 6 to 28 carbons; lauric acid, myristic acid, palmitic acid, stearic acid, oleic acid, linoleic acid, linolenic acid, arachidic acid, behenic acid, nervonic acid, and so forth may be cited as examples. Any one of these may be used alone, or any two or more of these may be used in combination. A saturated fatty acid having 14 to 20 carbons is more preferred. As the metal making up the fatty acid metal salt, potassium, sodium, and other such alkali metals; magnesium, calcium, barium, and other such alkaline earth metals; and zinc, nickel, molybdenum, and so forth may be cited as examples, preferred among which is zinc. Any one processing additive may be used alone, or two or more processing additives may be used in combination. For every 100 parts by mass of total rubber, the amount of processing additive that is added might, for example, be not less than 0.1 part by mass, it being preferred that this be not less than 0.3 part by mass. For every 100 parts by mass of total rubber, the upper limit of the range in values for the amount of processing additive that is added might, for example, be 5 parts by mass, it being preferred that this be 3 parts by mass. Other compounding ingredient(s) might, for example, be stearic acid, wax, zinc oxide, antioxidant, and/or the like. As examples of the antioxidant, aromatic-amine-type antioxidants, amine-ketone-type antioxidants, monophenol-type antioxidants, bisphenol-type antioxidants, polyphenol-type antioxidants, dithiocarbamate-type antioxidants, thiourea-type antioxidants, and the like may be cited. As the mixer, internal mixers, open roll mills, and the like may be cited as examples. As an internal mixer, Banbury mixers, kneaders, and the like may be cited as examples.

The tire member manufacturing method in accordance with the first embodiment further comprises an operation in which a vulcanizing-type compounding ingredient is added to the mixture, and in which the vulcanizing-type compounding ingredient is kneaded into the mixture to obtain a rubber composition. As examples of the vulcanizing-type compounding ingredient, sulfur, organic peroxides, and other such vulcanizing agents, vulcanization accelerators, vulcanization accelerator activators, vulcanization retarders, and so forth may be cited. As the sulfur, powdered sulfur, precipitated sulfur, insoluble sulfur, high dispersing sulfur, and the like may be cited as examples. As examples of the vulcanization accelerators, sulfenamide-type vulcanization accelerators, thiuram-type vulcanization accelerators, thiazole-type vulcanization accelerators, thiourea-type vulcanization accelerators, guanidine-type vulcanization accelerators, dithiocarbamate-type vulcanization accelerators, and so forth may be cited.

The rubber composition comprises a rubber component that comprises natural rubber. It is preferred that the amount of natural rubber be not less than 40 mass %, and more preferred that this be not less than 50 mass %, per 100 mass % of the rubber component. The upper limit of the range in values for the amount of natural rubber might, for example, be 100 mass %.

The rubber composition further comprises carbon black. For every 100 parts by mass of the rubber component, it is preferred that the amount of carbon black be not less than 10 parts by mass, more preferred that this be not less than 20 parts by mass, and still more preferred that this be not less than 30 parts by mass. For every 100 parts by mass of the rubber component, it is preferred that the amount of carbon black be not greater than 80 parts by mass, and more preferred that this be not greater than 60 parts by mass.

The rubber composition further comprises a compound according to Formula (I). For every 100 parts by mass of the rubber component, it is preferred that the amount of the compound according to Formula (I) be not less than 0.1 part by mass, and more preferred that this be not less than 0.5 part by mass. For every 100 parts by mass of the rubber component, it is preferred that the amount of the compound according to Formula (I) be not greater than 10 parts by mass, and more preferred that this be not greater than 8 parts by mass.

The rubber composition may further comprise stearic acid, wax, zinc oxide, antioxidant, sulfur, vulcanization accelerator, and/or the like. It is preferred that the amount of the sulfur, expressed as equivalent sulfur content, be 0.5 part by mass to 5 parts by mass for every 100 parts by mass of the rubber component. It is preferred that the amount of the vulcanization accelerator be 0.1 part by mass to 5 parts by mass for every 100 parts by mass of the rubber component.

The rubber composition may be employed in tread(s), sidewall(s), chafer(s), bead filler(s), and other such tire member(s).

A tire manufacturing method in accordance with the first embodiment comprises an operation in which a green tire equipped with a tire member made up of the rubber composition is made. The tire manufacturing method in accordance with the first embodiment further comprises an operation in which the green tire is heated. The tire obtained by the method of the first embodiment may be a pneumatic tire.

Variations on the first embodiment will now be described. Whereas the tire member manufacturing method in accordance with the first embodiment comprised an operation in which carbon black and rubber latex were mixed to obtain a carbon black slurry, a variation on the first embodiment comprises, instead of that operation, an operation in which carbon black and water are mixed to obtain a carbon black slurry.

A tire member manufacturing method in accordance with a second embodiment comprises an operation in which a compound according to Formula (I) is added to a mixture comprising carbon black and rubber. For every 100 parts by mass of the rubber, it is preferred that the amount of carbon black in the mixture be not less than 10 parts by mass, more preferred that this be not less than 20 parts by mass, and still more preferred that this be not less than 30 parts by mass. For every 100 parts by mass of the rubber, it is preferred that the amount of carbon black be not greater than 80 parts by mass, and more preferred that this be not greater than 60 parts by mass. The rubber might, for example, be natural rubber, isoprene rubber, butadiene rubber, styrene-butadiene rubber, nitrile rubber, chloroprene rubber, and/or the like. It is preferred that the amount of natural rubber in the mixture be not less than 70 mass %, more preferred that this be not less than 80 mass %, still more preferred that this be not less than 90 mass %, and still more preferred that this be 100 mass %, per 100 mass % of the rubber. The amount of the compound according to Formula (I) that is added might, for example, be 0.1 part by mass to 10 parts by mass for every 100 parts by mass of rubber within the mixture.

The tire member manufacturing method in accordance with the second embodiment further comprises an operation in which the compound according to Formula (I) is dispersed within the mixture in the presence of water to obtain a master batch. The amount of water in the mixture might, for example, be not less than 1 part by mass, it being preferred that this be not less than 10 parts by mass, for every 100 parts by mass of rubber within the mixture. The upper limit of the range in values for the amount of water in the mixture might, for example, be 800 parts by mass, it being preferred that this be 600 parts by mass. Regarding the master batch, the description given at the first embodiment is incorporated here.

The tire member manufacturing method in accordance with the second embodiment further comprises an operation in which master batch and peptizing agent and processing additive and/or other such compounding ingredients—and, where necessary, rubber not originating from the master batch—are dry-blended in a mixer to obtain a pre-addition-of-vulcanizing-type-compounding-ingredient mixture. Regarding this, the description given at the first embodiment is incorporated here.

The tire member manufacturing method in accordance with the second embodiment further comprises an operation in which a vulcanizing-type compounding ingredient is added to the pre-addition-of-vulcanizing-type-compounding-ingredient mixture, and in which the vulcanizing-type compounding ingredient is kneaded into the pre-addition-of-vulcanizing-type-compounding-ingredient mixture to obtain a rubber composition. Regarding this, the description given at the first embodiment is incorporated here.

A tire manufacturing method in accordance with the second embodiment comprises an operation in which a green tire equipped with a tire member made up of the rubber composition is made. As the tire member, tread(s), sidewall(s), chafer(s), bead filler(s), and the like may be cited as examples. The tire manufacturing method in accordance with the second embodiment further comprises an operation in which the green tire is heated. The tire obtained by the method of the second embodiment may be a pneumatic tire.

WORKING EXAMPLES

Working examples in accordance with the present disclosure are described below.

Raw materials and reagents are indicated below.

| | |
|---|---|
| Natural rubber latex (dry rubber content = 31.2%) | Manufactured by Golden Hope |
| Coagulant | Formic acid (reagent-grade 85%) manufactured by Nacalai Tesque, Inc. (diluted to obtain 10% solution and pH adjusted to 1.2 prior to use) |
| Carbon black | "SEAST SO" manufactured by Tokai Carbon Co., Ltd. |
| Compound 1 | (2Z)-4-[(4-aminophenyl)amino]-4-oxo-2-butene acid sodium (compound according to Formula (I')) manufactured by Sumitomo Chemical Co., Ltd. |
| Zinc oxide | "Zinc Oxide No. 1" manufactured by Mitsui Mining |
| Stearic acid | "LUNAC S-20" manufactured by Kao Corporation |
| Wax | "OZOACE 0355" manufactured by Nippon Seiro Co., Ltd. |
| Antioxidant | "6PPD" (N-phenyl-N'-(1,3-dimethylbutyl)-p-phenylenediamine) manufactured by Monsanto Company |
| Peptizing agent | "Noctizer SD" manufactured by Ouchi Shinko Chemical Industrial Co., Ltd. |
| Processing Additive 1 | "Aktiplast MS" (mixture of DBD and fatty acid zinc salt; DBD content = 5 mass % to 10 mass %; fatty acid primary constituent is saturated fatty acid having 18 carbons) manufactured by Rhein Chemie |
| Processing Additive 2 | "Aktiplast PP" (fatty acid zinc salt) manufactured by Rhein Chemie |
| Processing Additive 3 | "Struktol WB16" (mixture of calcium soap and saturated fatty acid amide) manufactured by S&S Japan Co., Ltd. |
| Sulfur | "5% Oil Treated Sulfur Powder" manufactured by Tsurumi Chemical Industry Co., Ltd. |
| Vulcanization accelerator | "Sanceler NS-G" (N-(tert-butyl)-2-benzothiazolesulfenamide) manufactured by Sanshin Chemical Industry Co., Ltd. |

Preparation of Wet Master Batch at Working Examples 1 Through 7 and at Comparative Examples 5 Through 8

Water was added at 25° C. to concentrated natural rubber latex to obtain a dilute natural rubber latex having a solids (rubber) concentration that was 0.52 mass %, and a natural rubber latex having a solids (rubber) concentration that was 28 mass %. 50 parts by mass of carbon black was added to 954.8 parts by mass of the dilute natural rubber latex, and a ROBO MIX manufactured by PRIMIX Corporation was used to agitate the post-addition-of-carbon-black dilute natural rubber latex to obtain a carbon black/natural rubber slurry. The carbon black/natural rubber slurry was added to the natural rubber latex having the solids (rubber) concentration that was 28 mass % in accordance with TABLE 1, and a mixer for household use manufactured by SANYO was used to agitate the post-addition-of-carbon-black/natural-rubber-slurry natural rubber latex at 11300 rpm for 30 min to obtain a pre-coagulation rubber latex. Formic acid serving as coagulant was added to the pre-coagulation rubber latex in an amount sufficient to achieve a pH of 4, and a filter was used to separate the coagulum from waste liquid. Compound 1 was added to the coagulum, and Compound 1 was dispersed within the coagulum as a Model V-02 screw press (squeezer-type single-screw dewatering extruder) manufactured by Suehiro EPM Corporation was used to dewater/plasticize at 180° C. the post-addition-of-Compound-1 coagulum. As a result of the foregoing procedure, a wet master batch was obtained.

Preparation of Wet Master Batch at Comparative Examples 1 Through 4, Comparative Example 9, and Comparative Example 11

Except for the fact that Compound 1 was not added to the coagulum, a procedure identical to that of Working Example 1 was used to obtain the wet master batch of Comparative Examples 1 Through 4, Comparative Example 9, and Comparative Example 11.

Preparation of Wet Master Batch at Comparative Examples 10 and 12

Except for the fact that the coagulum was substantially completely dewatered prior to addition of the Compound 1 to the coagulum, a procedure identical to that of Working Example 1 was used to prepare the wet master batch of Comparative Examples 10 and 12.

Preparation of Unvulcanized Rubber at the Various Examples

The compounding ingredients except for sulfur and vulcanization accelerator were added in accordance with TABLE 1, a Model B Banbury mixer manufactured by Kobe Steel, Ltd., was used to carry out kneading, and the rubber mixture was discharged. The rubber mixture was then kneaded together with sulfur and vulcanization accelerator in a Model B Banbury mixer to obtain unvulcanized rubber.

Mooney Viscosity Index

Mooney viscosity of the unvulcanized rubber as it existed immediately following manufacture was measured in accordance with JIS K-6300-1, the Mooney viscosity being shown as indexed relative to a value of 100 for Comparative Example 1. The lower the index the lower the Mooney viscosity and the more excellent the workability.

Storage Stability

Storage stability of unvulcanized rubber was evaluated based on the criterion of Mooney viscosity. More specifically, Mooney viscosity of the unvulcanized rubber as it existed immediately following manufacture was measured in accordance with JIS K-6300-1, and Mooney viscosity was measured again after storing the unvulcanized rubber for 3 months at standard temperature (23° C.±2° C.). Post-storage Mooney viscosity is shown as indexed relative to a value of 100 for the Mooney viscosity as it existed immediately following manufacture. The closer the index is to 100 the more excellent the storage stability of the unvulcanized rubber.

Combined use of Compound 1 and Processing Additive 1 caused improvement of storage stability. Use of Compound 1 alone caused improvement of storage stability in an amount corresponding to 10 points (see Comparative Example 1 and Comparative Example 5). Use of Processing Additive 1 alone caused worsening of storage stability in an amount corresponding to 1 point (see Comparative Example 1 and Comparative Example 2). On the other hand, combined use of Compound 1 and Processing Additive 1 caused improvement of storage stability in an amount corresponding to 18 points (see Comparative Example 1 and Working Example 1).

Processing Additive 1 was effective in suppressing the increase in Mooney viscosity that would otherwise have

TABLE 1

| | | | Comparative Example | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| Manufacture wet master batch | Parts by mass | Natural rubber (solids content) | 100 | 100 | 100 | 100 | 100 | 100 | 100 | 100 | 100 | 100 | 100 | 100 |
| | | Carbon black | 45 | 45 | 45 | 45 | 45 | 45 | 45 | 45 | 45 | 45 | 45 | 45 |
| | | Compound 1 | — | — | — | — | 2 | 2 | 2 | 2 | — | 2 | — | 2 |
| | Water content (parts by mass) of coagulum at time of addition of Compound 1 | | 200 | 200 | 200 | 200 | 200 | 200 | 200 | 200 | 200 | — | 200 | — |
| | Wa/Wb | | — | — | — | — | 100 | 100 | 100 | 100 | — | — | — | — |
| Manufacture unvulcanized rubber | Parts by mass | Wet master batch | 145 | 145 | 145 | 145 | 147 | 147 | 147 | 147 | 145 | 147 | 145 | 147 |
| | | Compound 1 | — | — | — | — | — | — | — | — | 2 | — | 2 | — |
| | | Zinc oxide | 3 | 3 | 3 | 3 | 3 | 3 | 3 | 3 | 3 | 3 | 3 | 3 |
| | | Stearic acid | 2 | 2 | 2 | 2 | 2 | 2 | 2 | 2 | 2 | 2 | 2 | 2 |
| | | Wax | 2 | 2 | 2 | 2 | 2 | 2 | 2 | 2 | 2 | 2 | 2 | 2 |
| | | Antioxidant | 2 | 2 | 2 | 2 | 2 | 2 | 2 | 2 | 2 | 2 | 2 | 2 |
| | | Peptizing agent | — | — | — | — | — | 0.2 | — | — | — | — | — | — |
| | | Processing Additive 1 | — | 2 | — | — | — | — | — | — | — | — | 2 | 2 |
| | | Processing Additive 2 | — | — | 2 | — | — | — | 2 | — | — | — | — | — |
| | | Processing Additive 3 | — | — | — | 2 | — | — | — | 2 | — | — | — | — |
| | | Sulfur | 1.5 | 1.5 | 1.5 | 1.5 | 1.5 | 1.5 | 1.5 | 1.5 | 1.5 | 1.5 | 1.5 | 1.5 |
| | | Vulcanization accelerator | 0.5 | 0.5 | 0.5 | 0.5 | 0.5 | 0.5 | 0.5 | 0.5 | 0.5 | 0.5 | 0.5 | 0.5 |
| | Mooney viscosity index | | 100 | 91 | 95 | 97 | 121 | 118 | 107 | 108 | 125 | 128 | 116 | 120 |
| | Storage stability index | | 120 | 121 | 122 | 123 | 110 | 102 | 111 | 109 | 118 | 116 | 120 | 117 |

| | | | Working Example | | | | | | |
|---|---|---|---|---|---|---|---|---|---|
| | | | 1 | 2 | 3 | 4 | 5 | 6 | 7 |
| Manufacture wet master batch | Parts by mass | Natural rubber (solids content) | 100 | 100 | 100 | 100 | 100 | 100 | 100 |
| | | Carbon black | 45 | 45 | 45 | 45 | 45 | 45 | 45 |
| | | Compound 1 | 2 | 2 | 2 | 2 | 2 | 2 | 2 |
| | Water content (parts by mass) of coagulum at time of addition of Compound 1 | | 200 | 4 | 10000 | 200 | 200 | 200 | 200 |
| | Wa/Wb | | 100 | 2 | 5000 | 100 | 100 | 100 | 100 |
| Manufacture unvulcanized rubber | Parts by mass | Wet master batch | 147 | 147 | 147 | 147 | 147 | 147 | 147 |
| | | Compound 1 | — | — | — | — | — | — | — |
| | | Zinc oxide | 3 | 3 | 3 | 3 | 3 | 3 | 3 |
| | | Stearic acid | 2 | 2 | 2 | 2 | 2 | 2 | 2 |
| | | Wax | 2 | 2 | 2 | 2 | 2 | 2 | 2 |
| | | Antioxidant | 2 | 2 | 2 | 2 | 2 | 2 | 2 |
| | | Peptizing agent | — | — | — | — | — | 0.2 | 0.2 |
| | | Processing Additive 1 | 2 | 2 | 2 | 1 | 3 | — | — |
| | | Processing Additive 2 | — | — | — | — | — | 2 | — |
| | | Processing Additive 3 | — | — | — | — | — | — | 2 |
| | | Sulfur | 1.5 | 1.5 | 1.5 | 1.5 | 1.5 | 1.5 | 1.5 |
| | | Vulcanization accelerator | 0.5 | 0.5 | 0.5 | 0.5 | 0.5 | 0.5 | 0.5 |
| | Mooney viscosity index | | 102 | 103 | 102 | 110 | 92 | 104 | 104 |
| | Storage stability index | | 102 | 101 | 101 | 103 | 102 | 103 | 102 | occurred due to Compound 1. Use of Compound 1 alone caused increase in Mooney viscosity in an amount corresponding to 21 points (see Comparative Example 1 and Comparative Example 5). Use of Processing Additive 1 alone caused decrease in Mooney viscosity in an amount corresponding to 9 points (see Comparative Example 1 and Comparative Example 2). On the other hand, combined use of Compound 1 and Processing Additive 1 caused increase in Mooney viscosity in an amount corresponding to a mere 2 points (see Comparative Example 1 and Working Example 1).

The invention claimed is:

1. A tire member manufacturing method comprising:
an operation in which a master batch is made; and
an operation in which the master batch and peptizing agent and processing additive are mixed;
wherein the operation in which the master batch is made comprises
an operation in which carbon-black-containing pre-coagulation rubber latex is coagulated to obtain a coagulum;
an operation in which a compound according to Formula (I), below, is added to the water-containing coagulum; and
an operation in which the compound is dispersed within the coagulum;
wherein Formula (I) is given by

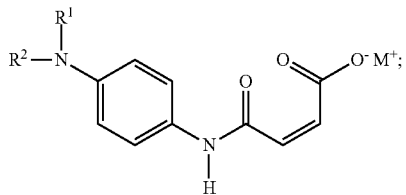

and
wherein, at Formula (I), $R^1$ and $R^2$ each indicates a hydrogen atom, an alkyl group having 1 to 20 carbons, an alkenyl group having 1 to 20 carbons, or an alkynyl group having 1 to 20 carbons;
$R^1$ and $R^2$ may be the same or different; and
$M^+$ indicates sodium ion, potassium ion, or lithium ion.

2. The tire member manufacturing method according to claim 1 wherein the operation in which the compound is dispersed within the coagulum is an operation in which the compound is dispersed within the coagulum as the coagulum is being dewatered.

3. The tire member manufacturing method according to claim 1 wherein,
at the operation in which the compound is added to the coagulum, taking the amount of water in the coagulum for every 100 parts by mass of rubber within the coagulum to be Wa, and taking the amount of the compound that is added for every 100 parts by mass of rubber within the coagulum to be Wb, Wa/Wb, being the ratio of Wa to Wb, is in a range that is 1 to 8100.

4. A tire manufacturing method comprising the tire member manufacturing method according to claim 1.

5. A tire member manufacturing method comprising:
an operation in which a master batch is made; and
an operation in which the master batch and peptizing agent and processing additive are mixed;
wherein the operation in which the master batch is made comprises
an operation in which a compound according to Formula (I), below, is added to a mixture comprising carbon black and rubber; and
an operation in which the compound is dispersed within the mixture in the presence of water;
wherein Formula (I) is given by

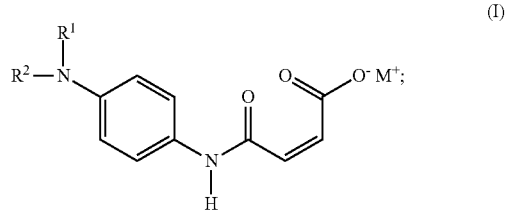

and
wherein, at Formula (I), $R^1$ and $R^2$ each indicates a hydrogen atom, an alkyl group having 1 to 20 carbons, an alkenyl group having 1 to 20 carbons, or an alkynyl group having 1 to 20 carbons;
$R^1$ and $R^2$ may be the same or different; and
$M^+$ indicates sodium ion, potassium ion, or lithium ion.

6. A tire manufacturing method comprising the tire member manufacturing method according to claim 5.

* * * * *